(12) United States Patent
Lindner

(10) Patent No.: US 8,373,756 B2
(45) Date of Patent: Feb. 12, 2013

(54) METHOD FOR TESTING A MONITORING DEVICE OF AN AUTOMATIC LABELING MACHINE FOR CORRECT FUNCTIONING

(75) Inventor: Peter Lindner, Langquaid (DE)

(73) Assignee: Krones AG, Neutraubling (DE)

( * ) Notice: Subject to any disclaimer, the term of this patent is extended or adjusted under 35 U.S.C. 154(b) by 541 days.

(21) Appl. No.: 12/589,819

(22) Filed: Oct. 29, 2009

(65) Prior Publication Data

US 2010/0110197 A1    May 6, 2010

(30) Foreign Application Priority Data

Oct. 31, 2008 (DE) .......................... 10 2008 054 238

(51) Int. Cl.
*H04N 7/18* (2006.01)
*G06F 15/16* (2006.01)

(52) U.S. Cl. ........................................ 348/161
(58) Field of Classification Search .................. 348/161, 348/135
See application file for complete search history.

(56) References Cited

U.S. PATENT DOCUMENTS

| | | | | |
|---|---|---|---|---|
| 3,883,385 A * | 5/1975 | Kirk et al. | ...................... | 156/352 |
| 4,270,863 A | 6/1981 | Trogdon | .......................... | 356/71 |
| 4,589,949 A | 5/1986 | Cavagnino | ..................... | 156/568 |
| 5,478,422 A | 12/1995 | Bright et al. | ..................... | 156/64 |
| 5,546,819 A | 8/1996 | Zodrow | ........................ | 73/865.8 |
| 6,597,804 B1 | 7/2003 | Heuft | ............................. | 382/142 |
| 7,328,558 B2 * | 2/2008 | Zwilling | .......................... | 53/544 |
| 2002/0087574 A1 * | 7/2002 | Walsh et al. | ................ | 707/104.1 |
| 2003/0210943 A1 * | 11/2003 | Nedblake et al. | ............. | 400/621 |
| 2005/0263443 A1 | 12/2005 | Martin et al. | ................. | 209/522 |
| 2006/0260276 A1 * | 11/2006 | Baldwin | ....................... | 53/137.2 |
| 2007/0113986 A1 * | 5/2007 | Harte | ............................ | 156/541 |
| 2007/0146474 A1 * | 6/2007 | Kameda et al. | ............... | 347/262 |
| 2008/0003043 A1 * | 1/2008 | Fukui et al. | ................ | 400/615.2 |
| 2008/0093448 A1 * | 4/2008 | de la Huerga | ................ | 235/385 |
| 2009/0316145 A1 | 12/2009 | Widera | ......................... | 356/240 |
| 2011/0164257 A1 | 7/2011 | Motter et al. | ................. | 356/614 |

FOREIGN PATENT DOCUMENTS

| | | |
|---|---|---|
| DE | 30 38 392 A1 | 5/1981 |
| DE | 33 14 730 C2 | 10/1984 |
| DE | 33 24 173 C1 | 1/1985 |
| DE | 33 24 449 A1 | 1/1985 |
| DE | 42 00 798 C2 | 7/1993 |
| DE | 43 02 656 C2 | 5/1994 |
| DE | 196 46 694 A1 | 5/1998 |
| DE | 299 10 452 U1 | 8/1999 |
| DE | 199 46 080 A1 | 5/2000 |
| DE | 199 11 074 B4 | 9/2000 |
| DE | 10 2006 022 492 A1 | 11/2007 |

(Continued)

OTHER PUBLICATIONS

Translation of claim 1 of DE 299 10 452U1 (1 page).

*Primary Examiner* — Zarni Maung
(74) *Attorney, Agent, or Firm* — Davidson, Davidson & Kappel, LLC

(57) ABSTRACT

A method for testing a monitoring device (20) of an automatic labeling machine (10) for containers (12) for correct functioning, in the case of which, a specially marked measuring container (14) is fed thereto, upon whose detection, a labeling process is discontinued at least for this measuring container (14), and the measuring container (14) provided with markings (16) is scanned by at least one optical sensing device (21) of the monitoring device (20).

17 Claims, 3 Drawing Sheets

FOREIGN PATENT DOCUMENTS

| | | |
|---|---|---|
| DE | 197 58 799 B4 | 3/2008 |
| JP | 2008-1 28 944 A | 6/2008 |
| WO | WO 2006/011803 A2 | 2/2006 |
| WO | WO 2010/040512 A1 | 4/2010 |

* cited by examiner

METHOD FOR TESTING A MONITORING DEVICE OF AN AUTOMATIC LABELING MACHINE FOR CORRECT FUNCTIONING

This claims the benefits of German Patent Application DE 10 2008 054 238.5, filed Oct. 31, 2008 and hereby incorporated by reference herein.

The present invention relates to a method for testing a monitoring device of an automatic labeling machine for correct functioning.

BACKGROUND

Labels are typically applied to beverage containers and bottles filled with beverages in a continuous process by automatic labeling machines which constitute part of a rotary machine used for bottling. Poorly or slantingly applied labels can signify a deficiency which, under unfavorable conditions, can lead to shut-down of the bottling machine. To be able to continuously check for correct placement and fixation of the labels, a camera, or optionally a plurality of cameras having subsequent image analysis can be configured downstream of the labeling machine.

A labeling machine of this kind can be inferred from the German Examined Specification DE 199 11 074 B4. In the case of this known device, the analyzed images from a camera configured downstream of the labeling station are not only used for monitoring for correct placement of the labels, rather, correction signals are also generated therefrom for controlling a correction device for the particular labeling station or for synchronizing a gripper cylinder and removal elements. Thus, to a certain degree, this known system allows for correction of the label placement during continuous operation of the machine.

However, the known monitoring devices are only able to function with the desired degree of reliability when they, themselves, are not out of alignment. To correctly position the camera that is customarily used and to calibrate, respectively initialize this position, test containers can be used, for example, which have a suitable test pattern that can be recognized by the camera and used by the downstream evaluation unit to check the camera settings.

Such a test container and a test arrangement for a control device for containers is discussed in the German Patent Application DE 10 2006 022 492 A1. The test container has a plurality of uniform horizontal marking rings on the container surface that are intersected by vertical markings, thereby forming a grid-type marking structure. With the aid of this marking structure, and by using a system for precise height adjustment of the test container, the camera can be calibrated and adjusted.

Problems can always arise during operation of a labeling machine when an undetected camera misalignment either results in a failure to detect improperly applied labels or in an insufficient or even faulty correction of the setting data used for applying the labels. Often the necessity for a repeated adjustment and subsequent recalibration of the camera can only be deduced by taking precise measurements of containers provided with labels. In this case, however, a multiplicity of containers having improperly glued-on labels may have already been considered to be acceptable and fed for further processing and/or packaging.

SUMMARY OF THE INVENTION

An object of the present invention is to devise a method which will make it possible to assess and test the sensing quality and/or precision of a monitoring device for an automatic labeling machine.

The present invention provides a method for testing a monitoring device of an automatic labeling machine for containers for correct functioning,
wherein a specially marked measuring container is fed thereto to the labeling machine, and, upon its detection, a labeling process is discontinued at least for this measuring container, and the measuring container provided with markings is scanned by at least one optical sensing device of the monitoring device.

To label containers, one frequently used design variant of a labeling device provides for them to be transferred via a spacing worm, evenly spaced apart from one another, to an infeed starwheel of the labeling machine. From this infeed starwheel, each individual container is slid onto a separate centering plate located on a rotating container table. This infeed starwheel is connected to the container table by way of a gear. The container table, which is set into rotation by a main gear, advances the containers through a processing section, for example, for labeling, brush-on, and label control processes, etc. It is self-evident that the method according to the present invention may also be used for other variants of conveying and/or labeling devices.

To achieve precise labeling, the container must normally be fixed in position and centered when passing through the processing section. To that end, each container is tightly clamped between the centering plate and a centering bell that is lowered from the top machine portion. To be able to ascertain an exact position of the containers, it may be useful to monitor the conveying units and devices, such as sensors, monitoring devices, labeling units and many others as well, via a machine position transducer or the like. Such a machine position transducer is coupled to the labeling machine in a way that allows it to provide each container with a label with the desired precision. In addition, such a position transducer may be used to determine the instantaneous position of each individual rotary table and thus of each individual container at any time.

A use of computer-controlled servomotors induces a defined rotation of the centering plate that may be required for the labeling and brush-on processes. These servomotors may drive the individual centering plates separately and thus render possible a precise adaptation of the labels.

If the exact positioning of the labels placed on the containers is to be checked along the further travel path of the containers, cameras coupled to an image analysis may be used at an appropriate location. For example, a location in the vicinity of a discharge starwheel of a rotary machine may be suited as a camera position. In the present context, a camera of this type is used for label control processes and thus to control for proper functioning of the labeling units and the cooperation thereof with the conveying devices. The label control that is integrated at the discharge starwheel and is used as a monitoring device makes it possible to detect incorrectly labeled or unlabeled containers that have been discharged for further processing. Once detected, these faulty containers can be separated out in response to a signal to this effect and be diverted, for example, via a discharge conveyor belt. Thus, the camera acts as an optical sensing device of the monitoring device for scanning the containers. The signals generated by an image analysis circuit downstream of the camera are transmitted to the discharge starwheel in a way that either permits a specific container to be transferred out or routed further to subsequent devices of the labeling machine. For this purpose, the present invention additionally includes a program for detecting and processing specially marked measuring containers that may be introduced into the labeling machine during operation, in order to be able to selectively scan these measuring containers using the sensing device, respectively the camera and, on the basis of the acquired imaging signal, to be able to check and assess the alignment thereof. The measuring container does not produce any errors during the labeling process. Rather, the labeling is discontinued or interrupted in response to the measuring container passing by, to allow scanning of the surface and/or structure thereof without any disturbing influences. Thus, a method is provided for testing the monitoring device of the automatic labeling machine for correct functioning.

It is important that the functions of the monitoring device be regularly checked in the manner described to be able to detect and rectify possible misalignments of the monitoring device as quickly as possible.

The optical sensing device may be constituted of at least one camera having downstream image analysis. However, a plurality of such cameras may also be provided at various machine positions. The at least one optical sensing device, respectively camera scans each container and, with the aid of the downstream image analysis, ascertains all possible errors of the imaging. By scanning and sensing the measuring container, correct image coordinates are then able to be assigned with the aid of the previously set container coordinates, making it possible to identify skewed or too high or too low placement of the markings of the measuring container in the imaging of the camera. To be able to regularly execute the test program in the labeling machine, one or even a plurality of specially marked measuring containers should be introduced into the running machine. These measuring containers are provided with defined, optically uniquely identifiable and assignable features to permit accurate recognition of a faulty imaging of the optical sensing device, respectively camera.

The measuring container preferably has a suitable identifying marking that is used for interacting with a sensor of the labeling machine, so that an introduced measuring container may be uniquely recognized as such. These features on the measuring containers could be constituted of an optical, magnetic, inductive and/or combination identifying marking; an RFID identifying marking is also conceivable. These identifying markings permit interaction with a corresponding sensor that may be mounted on the infeed starwheel of the labeling machine, for example, so that, in connection with the signal from the machine position transducer, the instantaneous position of the measuring container may be tracked and corresponding machine commands initiated at any time.

The optical markings of the measuring container are used exclusively for interacting with the optical sensing device, respectively the camera. Thus, the markings may be scaled, for example, through the use of a multiplicity of horizontal rings and vertical lines. This may be achieved, for example, by using black lines and/or engravings. The marking lines completely encircle the measuring container and are optionally spaced at the same or different intervals. These intervals are preferably adapted to the image analysis circuit of the monitoring device to enable the acquired measuring container images to be uniquely assigned to specific camera misalignments. Another possible embodiment of the measuring containers could provide for using a different color design to differentiate them from the other containers. Other variants would include introducing patterns, such as a black grid pattern or a colored checkered pattern.

Thus, it is highly important to detect the measuring container and determine its position since, at least for this measuring container, it is intended that the labeling process be interrupted at the labeling station and that the monitoring device check each recognized measuring container using its image coordinates. In addition, with the aid of the previously determined position, it should thereby be possible for the measuring container to be transferred out at a specified location once it has passed through. During its passage through the labeling machine, the position of the measuring container may be determined by at least one sensor at the infeed starwheel of the labeling machine. In addition, the position is determined by coordinating the centering plate with the position transducer of the machine, it being possible to additionally control other devices correspondingly.

Also, an additional sensor at a position downstream of the outward transfer [point] may monitor the passing-by of the measuring container. If the measuring container is detected as a result of the monitoring, an error signal may be subsequently generated which may lead, for example, to shut-down of the machine or to a repeated outward transfer process at another outward transfer position. If no further outward transfer position is provided, upon detection of the measuring container by the additional sensor, a stop signal for the labeling machine and/or for conveying devices configured upstream and/or downstream of the same may preferably be triggered.

It is worth mentioning that the feeding, detection and outward transfer of the measuring container take place during ongoing, uninterrupted operation of the labeling machine. The label feeding and affixing are separately controllable for each individual container. Upon detection of the measuring container as it passes by, the control of the label feeding and affixing is temporarily deactivated; the control is then reactivated for a subsequent container. This deactivation and activation of the label feeding and affixing processes may be carried out on the basis of the detected position of the measuring container that is also tracked during its passage through the labeling machine.

In accordance with another possible design variant of the method according to the present invention, the alignment and/or focusing of the at least one optical sensing device, respectively camera on the basis of the acquired measuring container images may be corrected during continuous operation of the labeling machine. Thus, depending on the adjustability of the camera, this may obviate the necessity of shutting down the entire machine, in the case that a faulty camera position and/or alignment are detected.

To record and/or check the function and setting of the at least one optical sensing device, the measuring container may be fed to the labeling machine as a function of time or as a function of the number of containers. This means that the measuring container may be repeatedly fed in, for example, following a defined processing time or following a specified number of containers that have already passed through the machine.

Other features, objectives and advantages of the present invention are derived from the following detailed description of a preferred specific embodiment of the present invention that is not to be considered as a limiting example and that makes reference to the enclosed drawing. In this context, the same components are basically denoted by the same reference numerals and, in part, are not explained multiple times.

DETAILED DESCRIPTION

Figure 1:
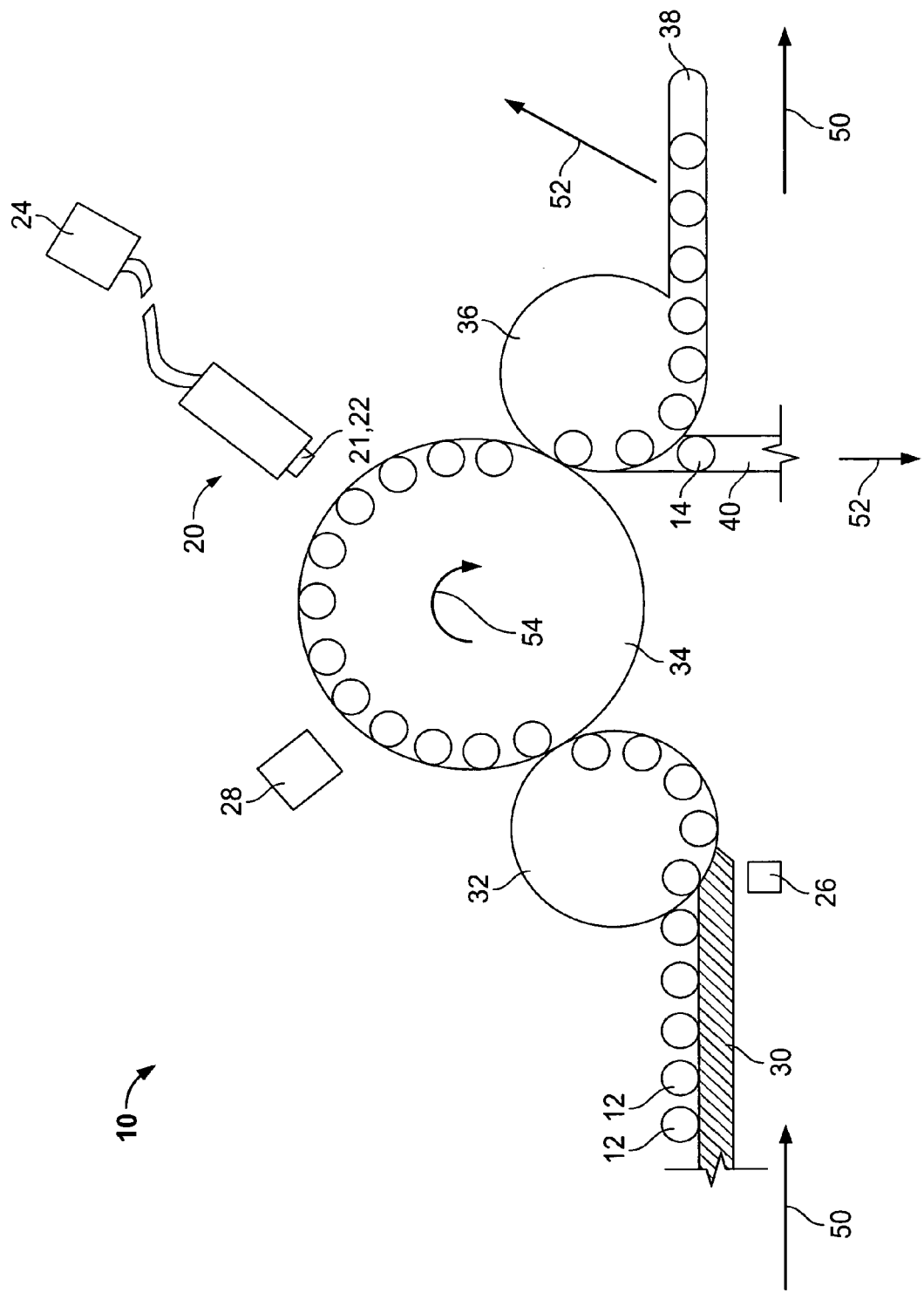
FIG. 1: shows a schematic configuration of a design variant of a labeling machine.

The schematic representation of FIG. 1 shows a typical configuration of a labeling machine 10 having an infeed starwheel 32 and a discharge starwheel 36, as well as a container table 34. Rotating spacing worm 30 spaces apart containers of container stream 12 arriving on a conveyor belt (not shown) in transport direction 50, by the requisite distance, without gaps, to ensure an error-free transfer into a recess in infeed starwheel 32 that is adapted to the container shapes.

Figure 2:
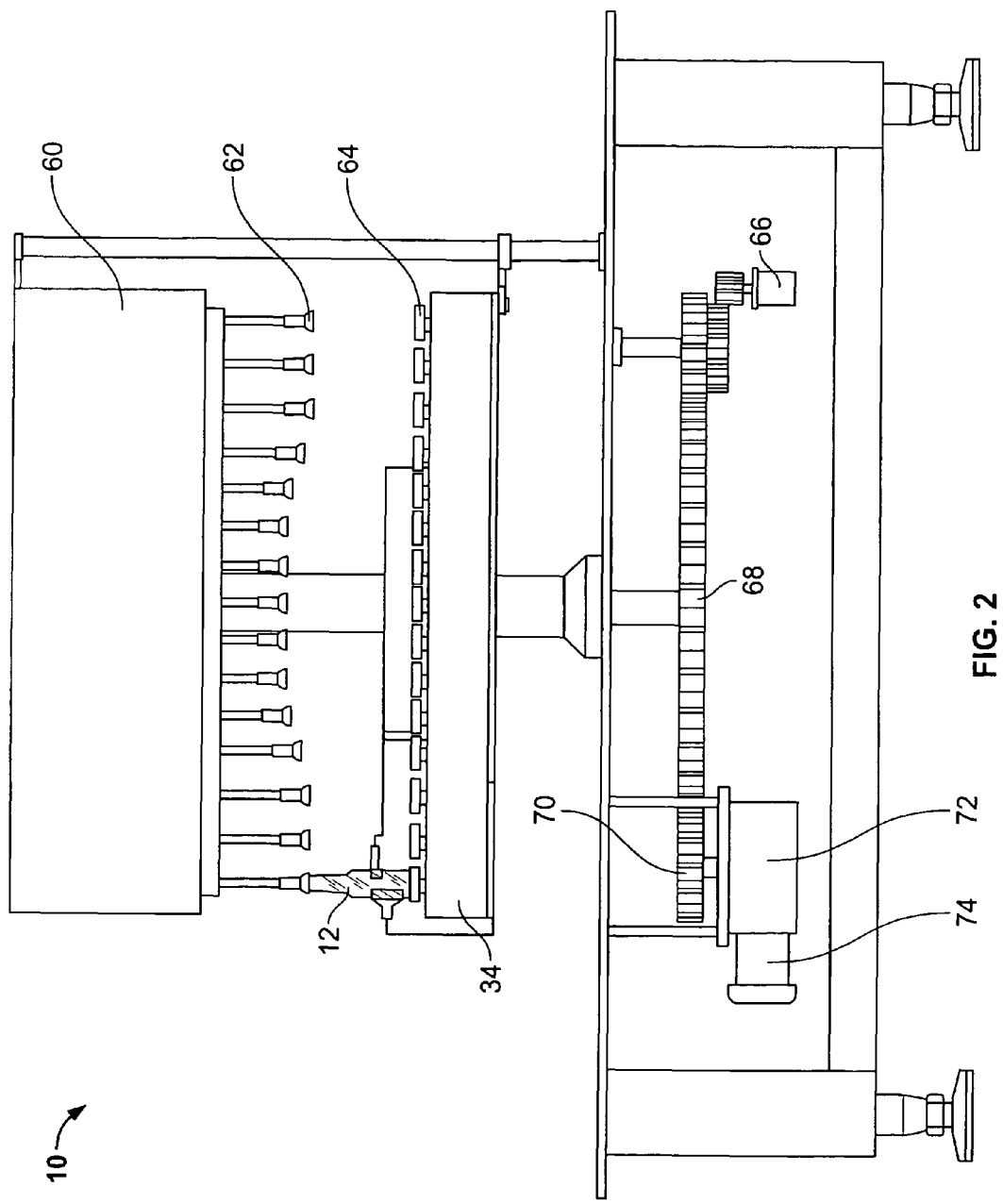
FIG. 2: shows a simplified specific embodiment of a container table of a rotary machine for labeling containers.

Infeed starwheel 32 transfers containers 12 to centering plates 64 which are mounted on container table 34 (compare FIG. 2). Container table 34 is set into rotation in clockwise direction 54. Containers 12 standing on centering plates 64 are moved past at least one labeling unit 28 and labeled. Marked measuring containers 14 likewise standing on centering plates 64 are recognized as such (as explained in greater detail in the following) and are not labeled at labeling unit 28. Using an optical sensing device 21 in the form of a camera 22, monitoring device 20 that follows ascertains the correct fixation or also, however, the possible absence of labels, and transmits the information to a downstream image analysis 24.

In the sensing of measuring container 14, this image analysis 24 has the task of comparing the current marking image of measuring container 14 to a stored reference image, using a reference measurement as a basis. On the basis of this comparison, the entire state of monitoring device 20 may be ascertained, and any discrepancies, such as a possible misalignment of camera 22, may at least be recognized. Depending on the machinery, such a detected camera misalignment may be compensated, when indicated, by an automatic realignment, for example. Alternatively, camera 22 may be manually aligned. To accomplish this, one of containers 12 may be replaced with a specially marked measuring container 14 that passes through machine 12 in the following manner. Relevant to the alignment of camera 22 is, first and foremost, the passage of such a marked measuring container 14.

Mounted just before the transfer of container 12 onto infeed starwheel 32 is a sensor 26 whose purpose is to detect a marked measuring container 14 which is to pass through machine 10 instead of a normal container 12. With the aid of sensor 26, the position and transfer of measuring container 14 may be precisely determined during its passage through machine 10. Sensor 26 is operatively connected to the at least one downstream labeling unit 28 and to monitoring device 20. In addition, a machine position transducer (compare FIG. 2) communicates the position of the containers to these devices.

The position coordinates of measuring container 14 are transmitted to labeling unit 28 in order to prevent measuring container 14 from being labeled in this case. Monitoring device 20 is able to recognize this measuring container 14, on the one hand, due to the absence of the label and, on the other hand, by scanning the contour of the bottle, respectively surface markings 16 thereof.

Containers 12 are individually transferred to discharge starwheel 36 during operation and are conveyed further in transport direction 50. Once detected, measuring container 14 is, in fact, also transferred to discharge starwheel 36, but is subsequently diverted onto a discharge conveyor belt 40. This discharge conveyor belt 40 may be situated at discharge starwheel 36 at a specified location or at a conveying device downstream therefrom.

Normally, only nonconforming containers 12 are loaded onto this discharge conveyor belt 40. In the present context, discharge conveyor belt 40 may be used to divert marked measuring containers 14 away from the further conveying process. Containers 12, respectively measuring containers 14, which have been separated out, are transported along a discharge path 52 and accumulated at a collection point (not shown), or they are deposited in a receptacle that has been set up.

FIG. 2 shows a simplified specific embodiment of a container table 34 of a rotary machine. Mounted on container table 34 are centering plates 64 on which containers 12, as well as marked measuring containers 14 (compare FIG. 3) may be carried further to individual processing stations, such as a labeling unit, labeling control, etc. (not shown). Containers 12, 14, which are transferred from infeed starwheel 32 to container table 34, are fixed in position and tightly clamped by a centering bell 62 and centering plate 64. Centering bell 62 is lowered from machine top portion 60 and grips containers 12, 14 around the bottlenecks thereof.

By way of a main gear 68, a machine position transducer 66 is in toothing engagement with container table 34. This main gear 68 is driven by a main drive gear 70 which, in turn, is driven by a main drive motor 74 via a gear unit 72. With the aid of machine position transducer 66, the position of each container 12, 14 on machine 10 is determined by a suitable monitoring circuit and, if indicated, made available as position signals to other control circuits.

Figure 3:
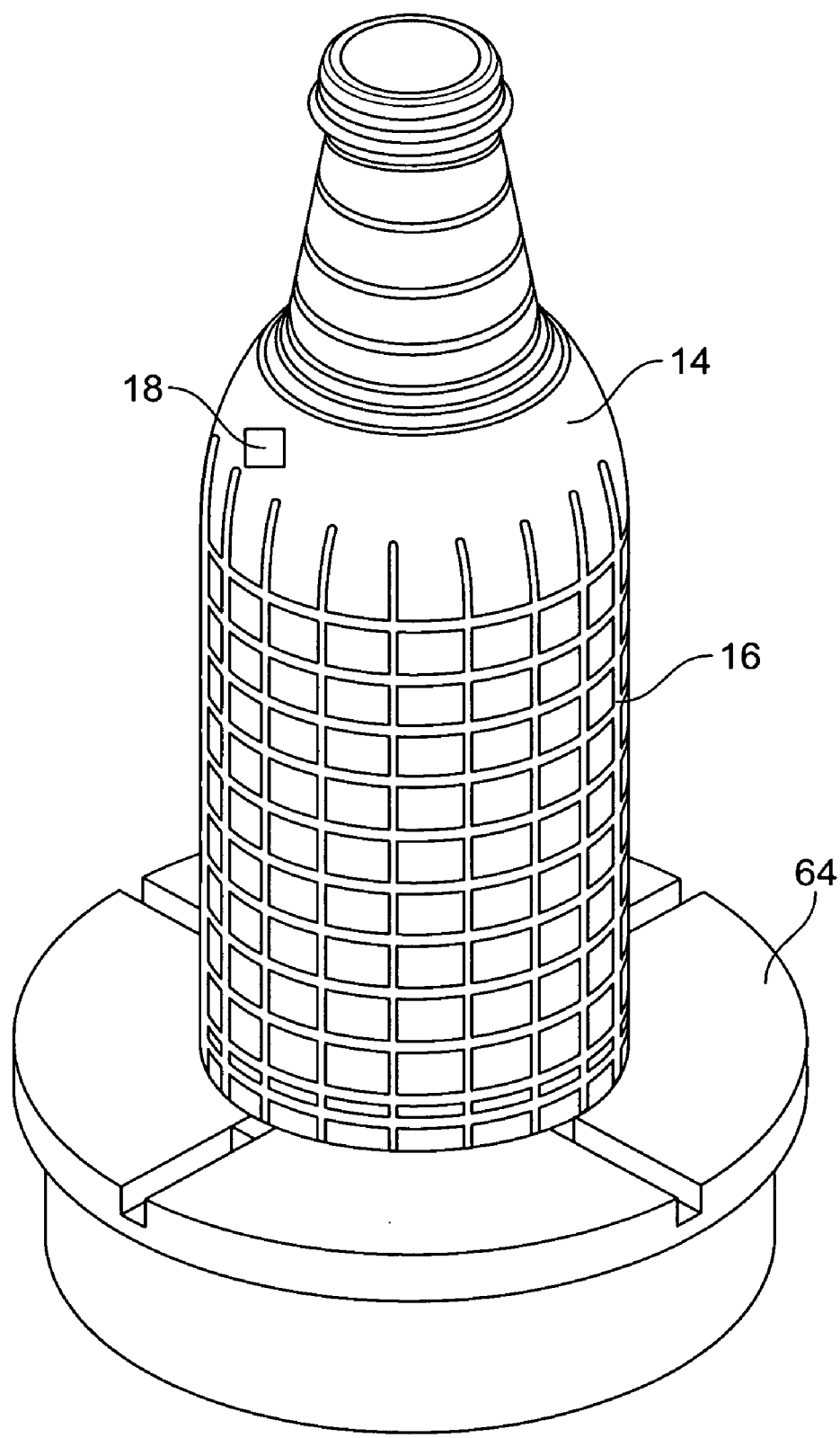
FIG. 3: shows one possible specific embodiment of a marked measuring container having optically identifiable markings.

One possible specific embodiment of a marked measuring container 14 is shown in FIG. 3. This specific embodiment shows one possible placement of markings 16. For example, horizontal marking rings and vertical marking lines may be introduced into an outer envelope surface of marked measuring container 14. These markings 16 may be optionally applied at regularly or irregularly spaced intervals.

Moreover, measuring container 14 has a uniquely identifiable marking 18 for interacting at least with sensor 26 (compare FIG. 1). This marking 18 may advantageously be formed by an RFID identifying marking or the like. Optical, magnetic, inductive and/or combination identifying markings 18 are possible, which, in each case, interact with the suitably configured, corresponding sensor 26 of labeling machine 10. In this manner, a measuring container 14 that is introduced into machine 10 may be uniquely identified as such, and its position may be tracked with the additional aid of machine position transducer 66 (compare FIG. 2). Labeling unit 28 is briefly deactivated as soon as measuring container 14 passes by to ensure that measuring container 14 does not receive a label and that its outer contour and markings 16 are able to be subsequently captured by camera 22.

The present invention is not limited to the preceding exemplary embodiments. Rather, a multiplicity of variants and modifications are conceivable that make use of the inventive idea and, therefore, likewise fall within the scope of protection.

What is claimed is:

1. A method for testing a monitoring device of an automatic labeling machine for containers for correct functioning, comprising:
   feeding a specially marked measuring container to the labeling machine, and, upon detection of the specially marked container, discontinuing a labeling process at least for the specially marked measuring container; and
   scanning the specially marked measuring container by at least one optical sensing device of the monitoring device.

2. The method as recited in claim 1 wherein, after passing by the optical sensing device at a specified location, the measuring container is diverted from the labeling machine or from a conveying device configured downstream therefrom.

3. The method as recited in claim 1 wherein the at least one optical sensing device includes a camera having downstream image analysis.

4. The method as recited in claim 3 wherein a plurality of cameras are provided for detecting the labeled containers at various machine positions.

5. The method as recited in claim 1 wherein the measuring container, to permit detection thereof, has an optical, magnetic, inductive and/or combination identifying marking for interacting with a corresponding sensor of the labeling machine.

6. The method as recited in claim 1 wherein the measuring-container, to permit detection thereof, has an RFID identifying marking for interacting with a corresponding sensor of the labeling machine.

7. The method as recited in claim 6 wherein, upon detection of the measuring container by the at least one sensor of the labeling machine, a position of the measuring container is determined and recognized during its passage through the labeling machine.

8. The method as recited in claim 7 wherein the measuring container is transferred out at an appropriate location of the labeling machine or of the conveying device configured downstream therefrom on the basis of the determination of the position of the measuring container upon the detection thereof by the at least one sensor.

9. The method as recited in claim 7 wherein the measuring container is transferred out at the appropriate location of the labeling machine or of the conveying device configured downstream therefrom on the basis of the position of the measuring container detected by the optical sensing device upon the scanning of the same.

10. The method as recited in claim 7 wherein an additional sensor at a position downstream of an outward transfer point monitors the passing-by of the measuring container and, upon detection of the measuring container, an error signal is generated.

11. The method as recited in claim 10 wherein, upon detection of the measuring container by the additional sensor, a stop signal for the labeling machine and/or for conveying devices configured upstream and/or downstream of the same is triggered.

12. The method as recited in claim 1 wherein the feeding, detection and outward transfer of the measuring container take place during ongoing, uninterrupted operation of the labeling machine.

13. The method as recited in claim 1 wherein label feeding and affixing are separately controllable for each individual container and, upon detection of the measuring container as the measuring container passes by, are temporarily deactivated, and are reactivated for a subsequent container.

14. The method as recited in claim 13 wherein the label feeding and affixing are deactivated and activated on the basis of the detected container position of the measuring container that is also tracked during passage through the labeling machine.

15. The method as recited in claim 1 wherein alignment and/or focusing of the at least one optical sensing device on the basis of the acquired images of the measuring container are corrected during continuous operation of the labeling machine.

16. The method as recited in claim 15 wherein the at least one optical sensing device includes a camera.

17. The method as recited in claim 1 wherein, to record and/or check the function and setting of the at least one optical sensing device, the measuring container is fed to the labeling machine at time intervals.

* * * * *